(12) United States Patent
Goldhaber et al.

(10) Patent No.: US 7,072,931 B2
(45) Date of Patent: Jul. 4, 2006

(54) ACCREDITATION MAINTENANCE THROUGH REMOTE SITE MONITORING

(76) Inventors: David Goldhaber, 128 N. El Camino Real, #213, San Mateo, CA (US) 94401; Mikhail Mineyev, 1428 Portola Dr., San Francisco, CA (US) 94127; Leon Kaufman, 161 4th Ave., San Francisco, CA (US) 94118

(*) Notice: Subject to any disclaimer, the term of this patent is extended or adjusted under 35 U.S.C. 154(b) by 686 days.

(21) Appl. No.: 09/860,030

(22) Filed: May 16, 2001

(65) Prior Publication Data

US 2002/0188652 A1  Dec. 12, 2002

(51) Int. Cl.
*G06F 15/16* (2006.01)
*G06Q 99/00* (2006.01)
*G06Q 10/00* (2006.01)
*G01B 5/28* (2006.01)

(52) U.S. Cl. .............................. 709/201; 705/1; 705/2; 702/39

(58) Field of Classification Search ........ 709/201–253; 702/39, 33–199; 378/207, 1–91; 73/1.01, 73/1.82, 865.9, 618, 619, 640, 570, 620, 73/866.4, 865.6; 128/915, 916, 922, 923; 705/2, 7–10, 28, 29
See application file for complete search history.

(56) References Cited

U.S. PATENT DOCUMENTS

| | | | |
|---|---|---|---|
| 5,655,084 A | 8/1997 | Pinsky et al. | |
| 5,995,937 A | 11/1999 | DeBusk et al. | |
| 6,122,351 A | 9/2000 | Schlueter, Jr. et al. | |
| 6,206,829 B1 | 3/2001 | Iliff | |
| 6,253,214 B1 | 6/2001 | Hall et al. | |
| 6,304,848 B1 | 10/2001 | Singer | |
| 6,347,329 B1* | 2/2002 | Evans | |
| 6,348,793 B1 | 2/2002 | Balloni et al. | |
| 6,370,480 B1* | 4/2002 | Gupta et al. | 702/39 |
| 6,412,980 B1* | 7/2002 | Lounsberry et al. | 378/207 |
| 6,430,536 B1* | 8/2002 | Irving et al. | |
| 6,739,877 B1* | 5/2004 | Bailey et al. | 434/262 |
| 2001/0032094 A1* | 10/2001 | Ghosh et al. | 705/1 |
| 2001/0032195 A1* | 10/2001 | Graichen et al. | |
| 2001/0051881 A1* | 12/2001 | Filler | |
| 2002/0069086 A1* | 6/2002 | Fracek et al. | |
| 2002/0133373 A1* | 9/2002 | Silva-Craig et al. | |
| 2002/0152096 A1* | 10/2002 | Falchuk et al. | |
| 2003/0140090 A1* | 7/2003 | Rezvani et al. | 709/203 |

OTHER PUBLICATIONS

American College of Radiology, Application Process for the Diagnostic Modality Accreditation Program, downloaded from \\Fileserver\accredmaster\UmbrellaProgram\Application ↑overview_reqs\dmap_overview.doc, pp. 1-8. Revision of Apr. 4, 2005.

(Continued)

*Primary Examiner*—David Wiley
*Assistant Examiner*—Arrienne M Lezak
(74) *Attorney, Agent, or Firm*—Townsend and Townsend and Crew LLP (57) ABSTRACT

Methods and systems for remotely monitoring an imaging facility's compliance with accreditation requirements. In a particular embodiment, the present invention remotely monitors the status of an MRI facility. In some configurations, the MRI unit is coupled to a server station. Information from the MRI unit is transmitted and stored on the server station. The information can be transmitted over a network, such as the internet, to a remote server. The remote server can collect and evaluate the accreditation data.

44 Claims, 8 Drawing Sheets

OTHER PUBLICATIONS

American College of Radiology, CT Accreditation Program Requirements, downloaded from W:\Umbrella Application\overview_reqs\reqs\ct_reqs.doc, pp. 1-15, Revision of Jun. 27, 2005.

American College of Radiology, CT Accreditation Program Requirements, downloaded from \\Fileserver\accredmaster\Umbrella Program\Application\overview_reqs\reqs\ct_reqs.doc, pp. 1-15. Revision of Oct. 17, 2004.

American College of Radiology, MRI Accreditation Program Requirements, downloaded from W:\Umbrella Program\Application\overview_reqs\reqs\mri_reqs.doc, pp. 1-12, Revision of Apr. 27, 2005.

American College of Radiology, Ultrasound Accreditation Program Requirements, downloaded from \\Fileserver\accredmaster\Umbrella Program\Application\overview_reqs\reqs\ultrasound_reqs.doc, pp. 1-8. Revision of May 25, 2005.

* cited by examiner

Center Frequency Log

Your name

Today's center frequency

Comments (optional)

[View Center Frequency Log]  [Log Today's Center Frequency]

Fig. 5

Center Frequency Log

Thank you, David, for logging today's center frequency.

Log Today's Center Frequency

Center Frequency Log

| Frequency | Name | Date & Time | Comments |
|---|---|---|---|
| 14.989898 | David | Tue Jan 30 17:34:01 2001 | |
| 14.006500 | Marsha | Thu Jan 18 11:36:57 2001 | manual override |
| 15.006500 | Marsha | Thu Jan 18 11:27:23 2001 | |
| 15.002726 | Joe | Wed Jan 17 11:43:49 2001 | |
| 15.002685 | Joe | Wed Dec 20 14:44:26 2000 | |
| 15.002776 | Joe | Tue Dec 19 12:05:16 2000 | |
| 15.002675 | Marsha | Thu Dec 14 08:11:41 2000 | |
| 15.002684 | Joe | Wed Dec 13 15:22:24 2000 | |
| 15.002786 | Joe | Tue Dec 12 08:27:01 2000 | |
| 15.002837 | Joe | Mon Dec 11 08:29:24 2000 | |
| 15.002767 | Marsha | Thu Dec 7 08:17:37 2000 | |
| 15.002777 | Joe | Wed Dec 6 07:43:00 2000 | |
| 15.002502 | Joe | Tue Nov 28 01:30:14 2000 | |
| 15.002471 | Marsha | Thu Nov 23 07:33:07 2000 | |
| 15.002471 | Joe | Wed Nov 22 08:48:26 2000 | |
| 15.002501 | Joe | Tue Nov 21 09:55:51 2000 | |
| 15.002289 | Marsha | Sat Nov 18 07:51:51 2000 | |
| 15.001200 | Joe | Wed Nov 15 05:38:42 2000 | |
| 15.001179 | Marsha | Sat Nov 11 09:16:26 2000 | |
| 15.001149 | Marsha | Fri Nov 10 09:00:48 2000 | |
| 15.001342 | Marsha | Thu Nov 9 03:16:08 2000 | |
| 15.001230 | Joe | Wed Nov 8 06:14:45 2000 | |
| 15.001231 | Joe | Tue Nov 7 08:25:06 2000 | |
| 15.001160 | Marsha | Fri Nov 3 08:08:30 2000 | |
| 15.001221 | Marsha | Thu Nov 2 06:36:15 2000 | |
| 15.001221 | Joe | Wed Nov 1 07:34:29 2000 | |
| 15.001210 | Joe | Tue Oct 31 07:10:28 2000 | |

Fig. 6

ACCREDITATION MAINTENANCE THROUGH REMOTE SITE MONITORING

BACKGROUND OF THE INVENTION

The present invention relates generally to methods and systems for monitoring remote facilities having imaging devices. In particular, the present invention relates to remotely monitoring Magnetic Resonance Imaging ("MRI") facilities to collect data for the American College of Radiology ("ACR") Accreditation Program.

Accreditation is a process whereby an imaging device operated within a remote facility is certified as meeting the standards set forth by an accreditation agency One such example, is the MRI Accreditation Program of the American College of Radiology ("ACR"). The accreditation process is a multi-component process that requires due diligence on the part of the personnel at the imaging facility to maintain their training, procedures and to maintain the high quality images of their MRI unit. The MRI Accreditation Program evaluates the qualifications of personnel, equipment performance, effectiveness of quality control measures, and quality of clinical images. A facility receiving ACR MRI Accreditation is awarded a three-year certificate of accreditation.

A growing number of health insurers and states (such as the Rhode Island) have begun requiring, MRI imaging facilities to become accredited with ACR to demonstrate to them (and their patients) their commitment to quality control.

The accreditation process for MRI comprise various components which must be completed successfully to receive accreditation. One component is a review of the credentials of physicians, physicists, technologists, personnel and other information common to the practice of MRI (i.e., safety measures, continuing education, or the like). Another component of the accreditation program involves the acquisition and quantification of clinical and phantom images and its corresponding data. Some examples of required clinical images include routine brain, cervical spine, lumbar spine, and knee examinations which have been acquired using specified sequences. The acquisition of phantom images involves the use of a designated MRI phantom. The required clinical and phantom images and corresponding data must be obtained from each full body general purpose magnet at the site of MRI practice. All the information collected and analyzed are then used in the accreditation process. ACR Accreditation will be granted to all participants whose accreditation material meet the criteria set forth by the ACR.

These components are then integrated into a submission package. Once a site is accredited, accreditation is predicated upon the site not undergoing major changes and maintaining a set of quality and operating control procedures. Such procedures require acquisition and maintenance of data on fixed schedules, including daily, monthly, twice-annual maintenance, continuing education of the personnel, and the like. The accreditation agency may visit and audit the site to evaluate the procedures and to determine if ACR procedures are being followed.

The collection, analysis, and documentation of the ongoing processes is a time consuming task. Over half of all initial applications submitted by the MRI centers are rejected. Several factors lead to the failures of the applications, including problems with imager performance, the choice of imaging parameters that are inappropriate for the anatomy or the imaging unit's field strength, and failure to follow the ACR's precise instructions for positioning and imaging the ACR test phantom. Accreditation activities distract the site personnel from pursuing the business of the site—which is to efficiently process patients. Consequently, it may be advantageous for an MRI site to contract this accreditation work to a third party, especially when the facility operates more than one imaging unit and/or has multiple physicians and other personnel. However, to satisfy the ACR requirements, the contractors would have to be at the MRI facility daily.

Therefore, what is needed are methods and systems for monitoring the accreditation process of a remote imaging facility. In particular, what is needed are methods for monitoring an MRI facility for its compliance with ACR accreditation requirements.

SUMMARY OF THE INVENTION

The present invention relates to methods and systems for remotely monitoring an imaging facility. In particular, the present invention provides methods and systems which monitor the accreditation status of a remote imaging site over a communication network, such as the internet.

In one aspect, the present invention provides a method of collecting accreditation information from an imaging facility. The method comprises transmitting information from the imaging facility over a network to a central server. The information received from the imaging facility is collated on a memory of the central server. Optionally, the information from the imaging facility is analyzed and compared to accreditation standards (either on site or at the central server) to help determine if the imaging facility is in compliance with accreditation standards. Thereafter, the analyzed information or status reports are transmitted back over the network to the imaging facility at periodic intervals to inform the imaging facility of their accreditation status.

Optionally, a third party can be present at the imaging facility to assist in the accreditation process (e.g., during the audit of the imaging facility, during the facility's preparation of the submission package, or the like). Because the accreditation information can be analyzed offsite (e.g., at the central server), a third party can analyze the accreditation information prior to physically visiting the imaging facility and the third party will have a better idea as to what remedial actions are necessary prior to visiting the imaging facility to maintain or acquire accreditation. Thus, instead of analyzing all of the accreditation data onsite for the first time to determine the facility's deficiencies, which can be a timely process, the third party can focus on the imaging facilities known deficiencies.

In another aspect, the present invention provides a method for monitoring an imaging facility from a remote location. The method comprises acquiring imaging information with an imaging device and other relevant information and transmitting the imaging information to a server station. The imaging information is sent from the server station over a network to a remote server where the information is saved on the remote server. It can then be remotely determined if the information from the imaging device is in compliance with accreditation requirements.

In a further aspect, the present invention provides a method for remotely monitoring an MRI facility for compliance with American College of Radiology recommendations and requirements. The method comprises acquiring information with the MRI device and from the facility operators and saving the information on a server station memory. The information is transmitted from the server station over a network to a central server where the information is saved on the central server. In another embodiment, the methods of the present invention can be used to remotely monitor a CT facility for compliance with accreditation recommendations and requirements.

The systems of the present invention typically include an imaging facility coupled to a communication network, such as the internet. By coupling the imaging facility to a communication network the images obtained by the imaging device in the facility and reports regarding the images can be remotely stored and analyzed to determine the accreditation status of the imaging facility. By storing the imaging data remotely the analysis of the accreditation data can be performed off site by third parties, thus allowing the personnel at the imaging facility to focus on their patients, instead of having to continuously track imaging information for accreditation purposes.

In exemplary embodiments, the remote imaging facility is equipped with an MRI unit that can capture images that is coupled to an internal network via a server station on which the phantom or clinical images can be stored. The server station can also be used to store other accreditation data such as preventive maintenance visit information, continuing education courses for the site physicians, technologists, personnel, or the like. An imaging study can be produced and attached to the image files or saved as a separate file on the server. The server can then encrypt and compress the images and studies for delivery over another communication network, such as the internet. The server can be programmed to transmit the encrypted data to a central server, where the information can be collated and analyzed for accreditation purposes or other purposes.

Transmission of the data from the server station to the central server can be accomplished in a variety of ways. For example, the server can be remotely directed to transmit data to the central processing server, documentation center, or another outside contractor. In another embodiment, the server automatically transmits data at appropriated intervals. In yet another embodiment, the server is queried by a contractor personnel over a network. In yet another embodiment, the contractor queries the server at appropriate intervals.

In addition to allowing for remote monitoring for accreditation, the servers of the present invention can be used in a variety of other ways to enhance the stations operations. For example, the servers can be attached to the facility's internal network for internal distribution among the physicians and other personnel within the imaging facility. Access to the images and reports can be accessed using a standard web-browser (such as Microsoft Internet Explorer), or other software capable of viewing the data stored on the imaging workstation The server station can be linked to the internet for worldwide access and distribution of image data. External access to the images and reports can be accessed using a standard web-browser (such as Microsoft Internet Explorer), or other software capable of viewing the data on the server. Therefore, reading physicians can access the server to collect images for remote review and referring physicians can receive images and reports directly onto their desktop PC's. Post-processed images generated by the imaging workstations can be supported, thereby enabling delivery of post-processed images via the internet. Such a connection can be used to connect the remote center with a specialist far away—either to broaden the range of services offered, or to take advantage of remote consultation with expert advisors for unusual cases.

The server station can be selectively programmed to give access only to targeted third parties. Typically, a login identification and password will be required to access the server. For example, if access is given to a particular patient, the patient's access can be limited to only that patient's particular files and images.

Optionally, because server station is connected to the communication network, the accreditation agency may be able to remotely monitor the imaging facility over the network and/or to perform its accreditation audits over the network. Moreover, it may be possible to electronically file the accreditation submission package over the communication network with the accreditation agency.

While the following discussion focuses on the monitoring and accreditation of MRI facilities, the present invention is applicable to other modalities than MRI. For example, the methods and systems of the present invention are also applicable to x-ray, CT, nuclear medicine, and to accreditation by any agency that may require periodic quality assurance procedures. For a further understanding of the nature and advantages of the invention, reference should be made to the following description taken in conjunction with the accompanying drawings.

DESCRIPTION OF THE SPECIFIC EMBODIMENTS

The present invention provides systems and methods for collecting, analyzing and documenting the ongoing status of an imaging facility. In particular, the present systems and methods are for tracking the imaging quality of an MRI imaging unit. The remote monitoring can be used to measure the accreditation status of the MRI imaging unit and can remotely alert the personnel at the imaging facility of any deficiencies or variances from accreditation requirements. If desired, the information collected from the MRI imaging unit can then be organized for submission into an accreditation agency, such as the American College of Radiology ("ACR") to gain and maintain accreditation for the imaging facility.

According to an exemplary embodiment of the present invention, methods and systems are disclosed for remotely monitoring an imaging facilities accreditation status. The types of information monitored may be customized based upon the accreditation data required by the accreditation agency. For example, the information collected and monitored for an MRI facility may differ from the types of information monitored for a CT facility.

Figure 1A:
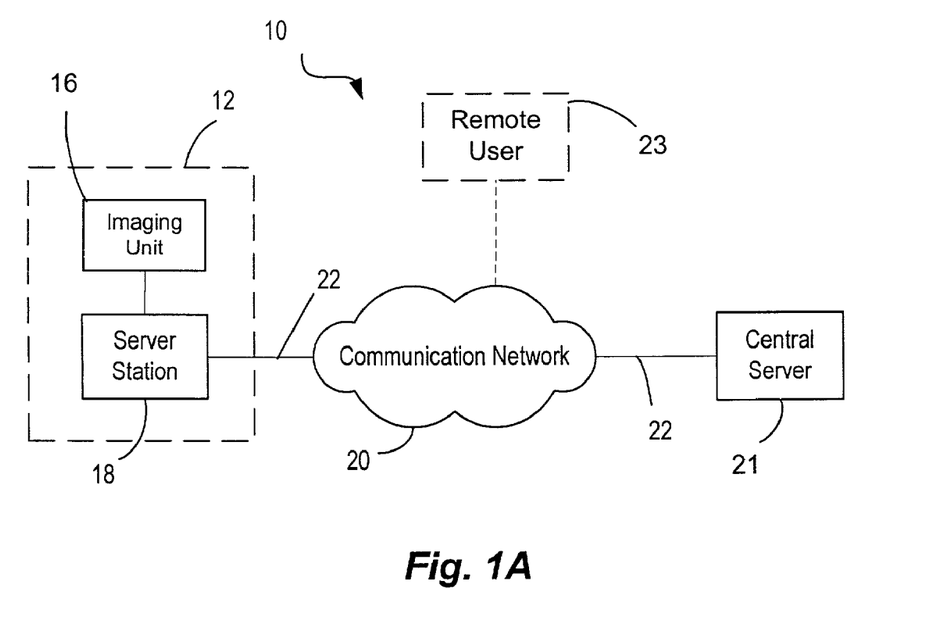
FIG. 1A is a simplified block diagram of a distributed system of the present invention.

As shown schematically in FIG. 1A, the communication systems 10 of the present invention generally include a remote imaging facility 12 that has at least one imaging unit 16 such as an MRI unit, a CT unit, a nuclear imaging unit, an X-ray unit, or the like. The imaging unit is typically coupled to or integral with a computer server station 18 that is connected to a communication network 20 via at least one communication link 22. Communication network 20 provides a mechanism for allowing the various components of the communication system 10 to communicate and exchange information with each other. The communication network 20 allows the server station 18 to communicate with a remote (or local) central server 21 and/or other remote users 23, such as patients, consultants, reviewing physicians, referring physicians, or the like.

Communication network 20 may itself be comprised of many interconnected computer systems and communication links. Communication links 22 may be hardwire links, optical links, satellite or other wireless communication links, wave propagation links, or any other mechanisms for communication of information. While in one embodiment, communication network 20 is the Internet, in other embodiments, communication network 20 may be any suitable computer network, such as an intranet, a local area network (LAN), a metropolitan area network (MAN), a wide area network (WAN), or the like.

Figure 1B:
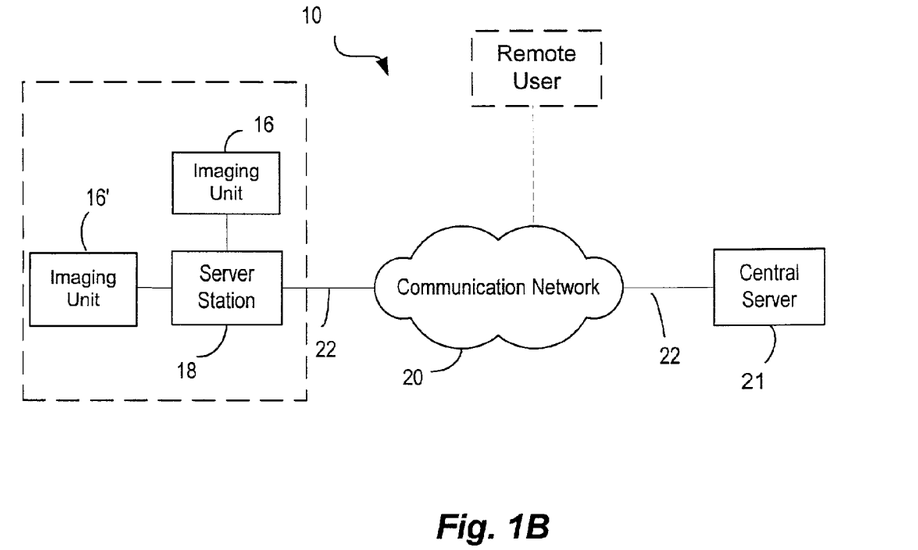
FIG. 1B illustrates a simplified block diagram of another embodiment of the system of the present invention.

The distributed computer network of system 10 depicted in FIG. 1A is merely illustrative of an embodiment incorporating the present invention and does not limit the scope of the invention as recited in the claims. While the imaging workstations depicted in FIG. 1A includes a computer server station 18 that is coupled to the imaging unit 16 one of ordinary skill in the art would recognize other variations, modifications, and alternatives. For example, as shown in FIG. 1B, a plurality of imaging units can be coupled to a single server station 18. Alternatively, each imaging facility 12 can include a plurality of server stations and imaging units (not shown). Moreover, while the server station and imaging unit are illustrated as separate entities, it should be appreciated that the server station 18 and imaging unit 16 can be integrated together as a single apparatus.

Figure 1C:
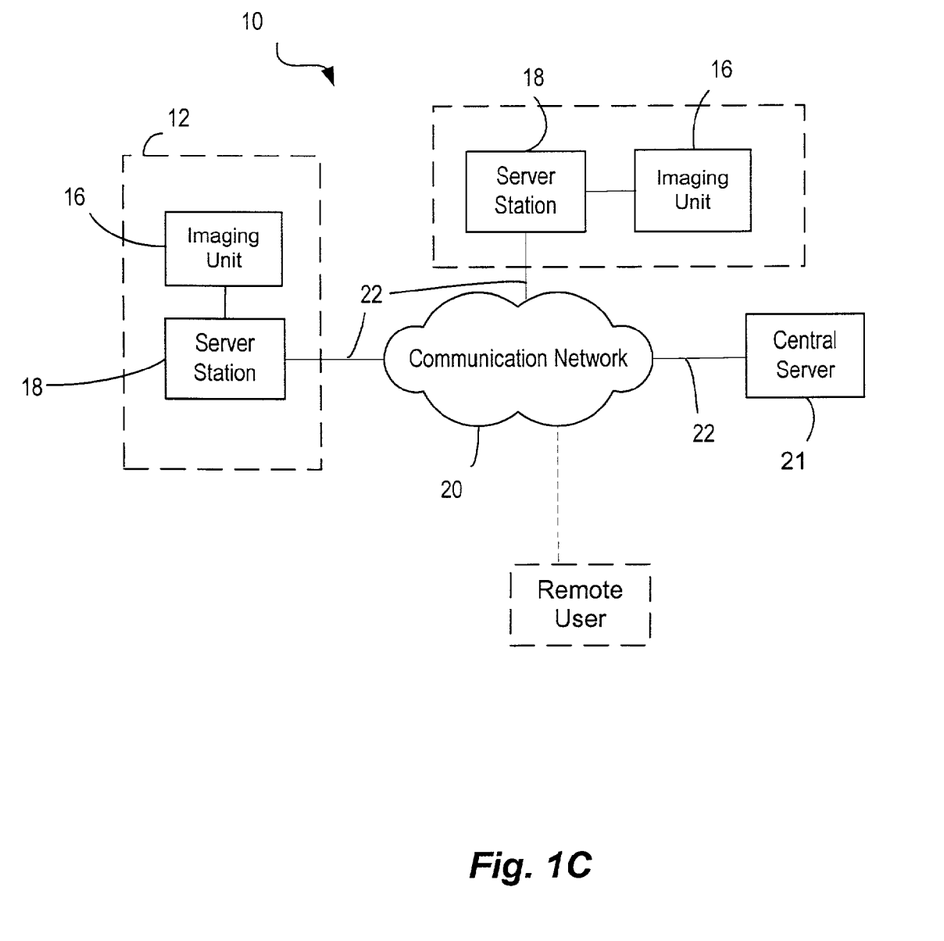
FIG. 1C illustrates a simplified block diagram of yet another embodiment of the system of the present invention.

As shown in FIG. 1C, a plurality of imaging facilities 12, 12' can be connected to the communication network 20. Each of the imaging facilities can be monitored concurrently by the central server(s) 21 to monitor their image quality and accreditation status. As will be described in detail below, each of the imaging facilities can have a web page, web site, or even a separate central server that is dedicated to that specific imaging facility 12. Consequently, each of the websites and servers can be programmed to allow only specified personnel, physicians, physicists, or the like to access and view the information related to the specific imaging facility.

Figure 2:
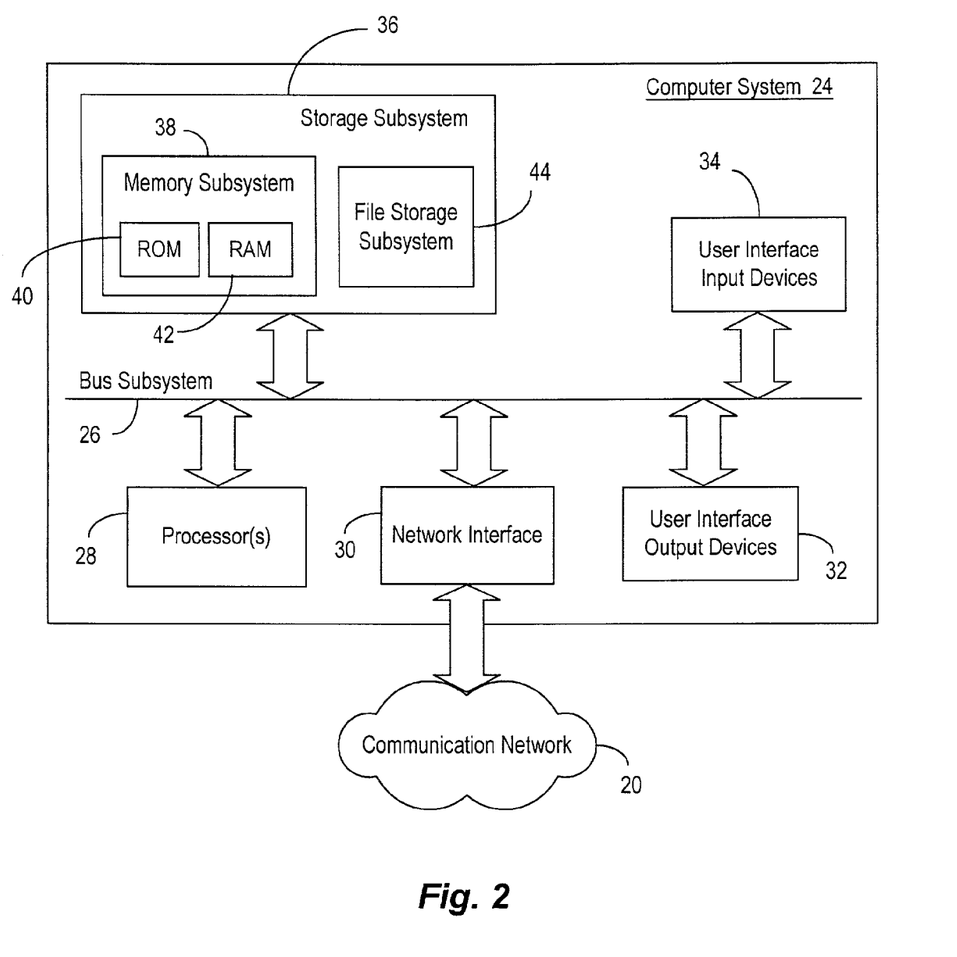
FIG. 2 illustrates an exemplary computer system according to an embodiment of the present invention.

FIG. 2 is a simplified block diagram of an exemplary computer system 24 incorporated by server station 18 and/or central server 21. Computer system 24 typically includes at least one processor 28 which communicates with a number of peripheral devices via a bus subsystem 26. These peripheral devices may include a storage subsystem 36, comprising a memory subsystem 38 and a file storage subsystem 44, user interface input devices 34, user interface output devices 32, and a network interface subsystem 30. Network interface subsystem 30 provides an interface to outside networks, including an interface to communication network 20, and is coupled via communication network 20 to corresponding interface devices in other computer systems.

User interface input devices 34 may include a keyboard, pointing devices such as a mouse, trackball, touch pad, or graphics tablet, a scanner, foot pedals, a joystick, a touch-screen incorporated into the display, audio input devices such as voice recognition systems, microphones, and other types of input devices. In general, use of the term "input device" is intended to include a variety of devices and ways to input information into computer system 24 or onto computer network 20.

User interface output devices 32 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide non-visual display such as via audio output devices. In general, use of the term "output device" is intended to include a variety of devices and ways to output information from computer system 24 to a user or to another machine or computer system.

Storage subsystem 36 stores the basic programming and data constructs that provide the functionality of the various embodiments of the present invention. For example, database and modules implementing the functionality of the present invention may be stored in storage subsystem 36. These software modules are generally executed by processor 28. In a distributed environment, the software modules may be stored on a plurality of computer systems and executed by processors of the plurality of computer systems. Storage subsystem 36 typically comprises memory subsystem 38 and file storage subsystem 44.

Memory subsystem 38 typically includes a number of memories including a main random access memory (RAM) 42 for storage of instructions and data during program execution and a read only memory (ROM) 40 in which fixed instructions are stored. File storage subsystem 44 provides persistent (non-volatile) storage for program and data files, and may include a hard disk drive, a floppy disk drive along with associated removable media, a Compact Digital Read Only Memory (CD-ROM) drive, an optical drive, or removable media cartridges. One or more of the drives may be located at remote locations on other connected computers at other sites coupled to communication network 20. The databases and modules implementing the functionality of the present invention may also be stored by file storage subsystem 44.

Bus subsystem 26 provides a mechanism for letting the various components and subsystems of computer system 24 communicate with each other as intended. The various subsystems and components of computer system 24 need not be at the same physical location but may be distributed at various locations within distributed network 10. Although bus subsystem 26 is shown schematically as a single bus, alternate embodiments of the bus subsystem may utilize multiple busses.

Computer system 24 itself can be of varying types including a personal computer, a portable computer, a workstation, a computer terminal, a network computer, a module in the imaging unit, a mainframe, or any other data processing system. Due to the ever-changing nature of computers and networks, the description of computer system 24 depicted in FIG. 2 is intended only as a specific example for purposes of illustrating the preferred embodiment of the present invention. Many other configurations of computer system 24 are possible having more or less components than the computer system depicted in FIG. 2.

Server station 18 of the present invention enables users at the imaging facility 12 and remote users 23 to access various resources distributed within communication system 10 and on central server 21. These resources include images, image data, and web pages stored by web sites which are hosted by server station 18 or central server 21. Using a browser, a user at the imaging facility 12 or a third party at a remote site 23 may retrieve and view web pages stored by the central server 21, or the like. Central server systems 21 can host one or more web sites which can be accessed by remote users 23 and personnel at the imaging facility 12. In some embodiments a separate web site is dedicated to each server station 18 or imaging facility 12. The remote users and personnel can access the phantom images, clinical images, clinical reports, phantom reports, statistics of daily-measured quality assurance parameters such as signal-to-noise ratios, maintenance logs, or a combination thereof through the website. Optionally, the web site can be secured to allow only selected third party users and personnel of the imaging facility 12 to access the web site. Some third parties may be given access to only certain portions of the web site. Thus, if a patient or consulting physician wanted to view the clinical images, they could be given an identification and password that allows them to access only the images and image data that is relevant to their needs, while keeping the other information secure. It should be appreciated that the central server may be customized for each server station to limit the access of information to the remote users.

Figure 3:
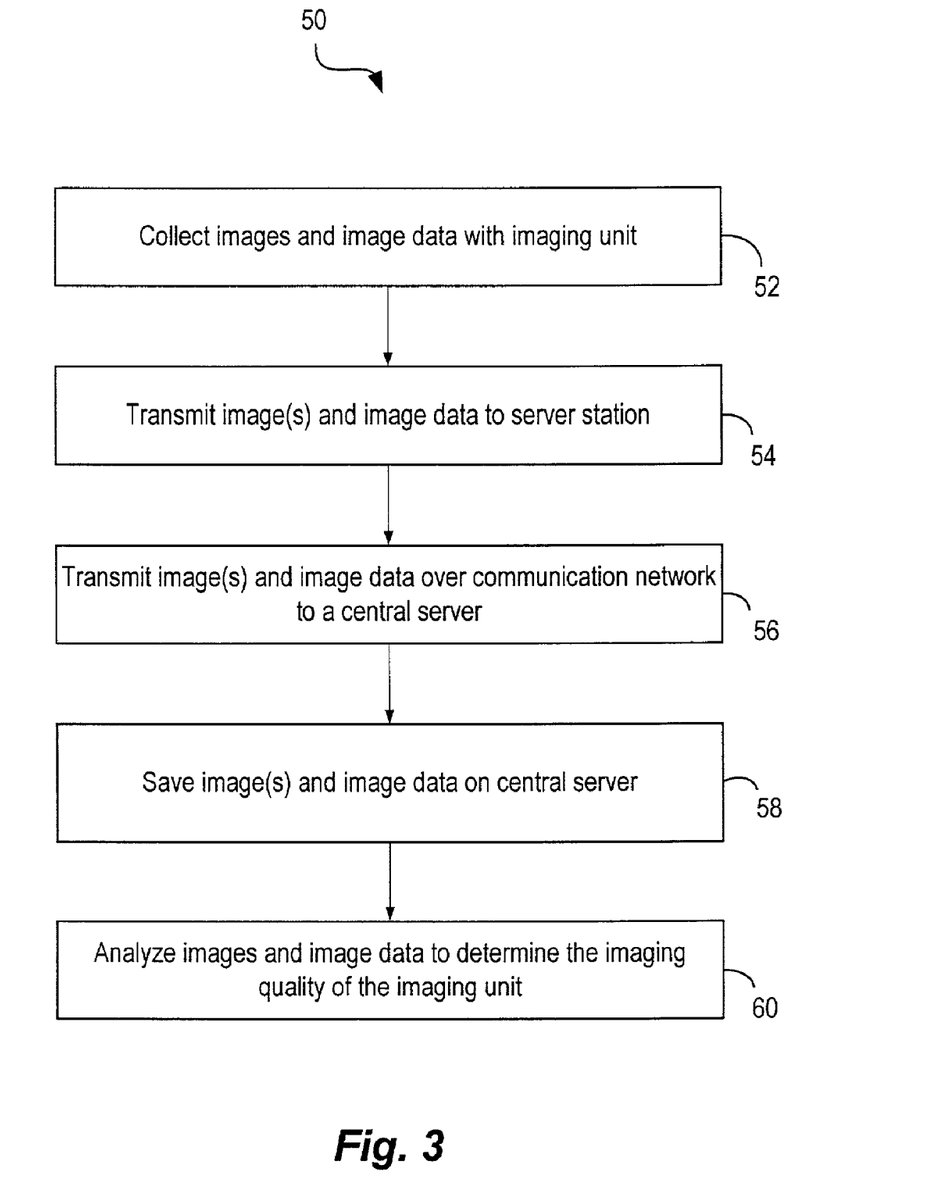
FIG. 3 illustrates a simplified flowchart showing an exemplary method of the present invention.

FIG. 3 illustrates an exemplary method 50 of the present invention. The methods of the present invention provide for remote monitoring the imaging quality of the imaging units. Image(s) and image data can be collected with the imaging unit (Step 52). For example, an ACR phantom image or clinical image can be imaged to track the image quality of the image station. The image(s) and image data can then be transmitted to and stored on a server station (Step 54). Optionally, if desired personnel of the imaging facility can manually input additional information into the server station, such as patient information, continuing education credits, maintenance visits and procedures, changes to site policies and procedures, or the like. The image(s) and image data (and the additional information) can then be transmitted over the communication network to the central server (Step 56). The image(s) and image data are saved on the central server, where they can be analyzed to determine the image quality of the imaging unit and the quality of procedures of the facility (Steps 58,60). Optionally, periodic reports or alerts can be transmitted over the communication network to the image workstation to inform the server station of the image quality. As will be discussed below, the periodic report can include information about the image quality, personnel training requirements, maintenance updates, or the like.

Figure 4:
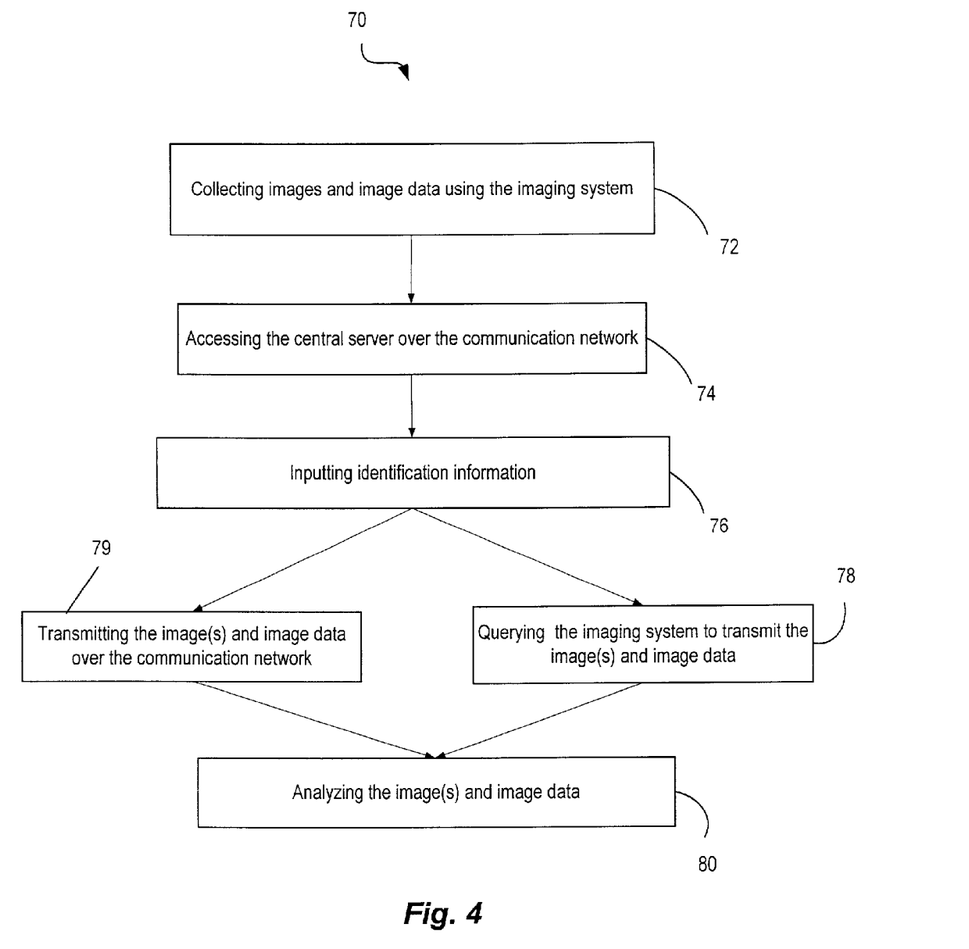
FIG. 4 illustrates a simplified flow chart illustrating an exemplary method of the present invention.

FIG. 4 illustrates an exemplary method for monitoring MRI Accreditation of a remote MRI imaging facility. This exemplary method is typically initiated when a user first starts operation of the imaging unit 12 A phantom image, typically supplied by the accreditation agency, is run through the imaging unit 16 (Step 72). Alternatively, in other methods, clinical images are filmed under certain specified conditions set forth by the accreditation agency. An output image is produced which can be saved on a server station memory. Once the images and image data are stored, the central server is accessed over the communication network (Step 74) and the information can be transmitted to the central server 21 using a variety of methods (Steps 78, 79). Thereafter, the images and image data can be analyzed at the server station and/or the central server (Step 80).

The server station 18 can be programmed to automatically transmit the information to the central server 21 over the communication network at appropriate intervals. The type of information stored on the server station will generally determine the interval of transmission. Certain imaging characteristics must be monitored continuously, while other imaging characteristics need only be monitored on a weekly, monthly, or semi-annual basis.

In another variation, the central server can be programmed to automatically query the server station 18 over the communication network at appropriate intervals so the central server 21 can upload the information over the communication network. For example, at the beginning of each day the central server may remotely query the server station over the communication network to determine the daily central resonant frequency of the server station. It should be appreciated that it may be beneficial to have a continuous communication link over the network between the central server and the server station so that continuous monitoring of the imaging quality can take place.

In other embodiments, personnel at the server station can manually query the central server 21 to initiate the transmission of data to the central server. Personnel at the imaging facility can access a hypertext page, otherwise known as a web page, over the Internet. These web pages are usually written in Hypertext Markup Language ("HTML") and may have any combination of text, data entry fields, images, video, or audio content. Each page is typically identified by an address called a Uniform Resource Locator ("URL") that enables users of the Internet to access the web page. Web pages are typically stored at web sites on computer systems, such as the central server 21. Using a browser program executing on the server station 18, the personnel at the imaging facility 12 can access a web page on the central server 21 and manually activate the transmission of information to the central server 21. The user can manually connect to the web page by providing the URL information for the web page stored on the remote central server or the user can click on a link to the web page. Once the web page is accessed, the user may be prompted to enter data, such as identification data (i.e., who they are or the identification of the imaging facility).

The web page accessed can be a "homepage" of the central server that may be accessed by a remote user. The user will typically be prompted to enter identification data so as to inform the central server where to store the information or what folders to access on the server. Alternatively, the web page accessed can be a web page dedicated to a single imaging facility or server station. The web page may be password protected or otherwise secured so as to allow only specified users to access, download, or upload information into the central server database.

Figure 5:
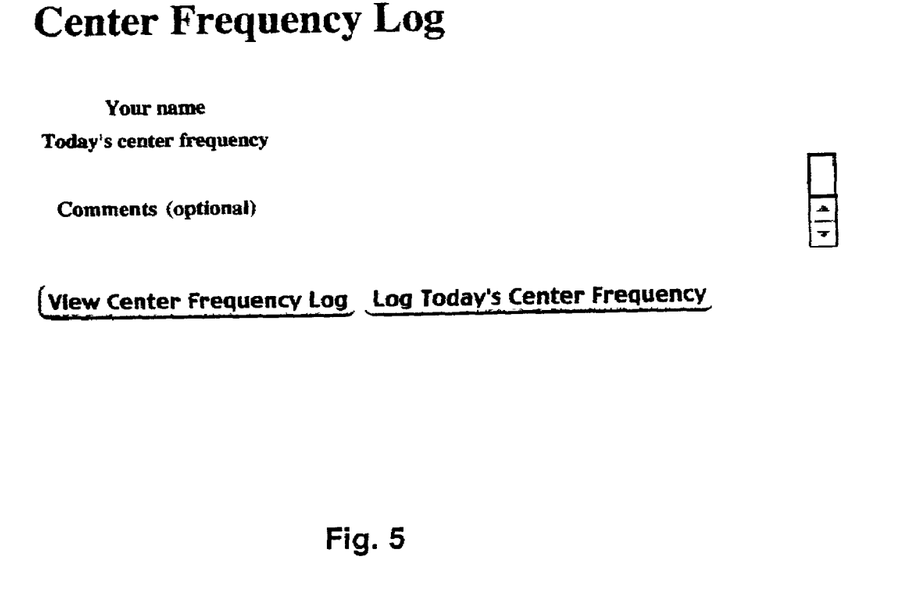
FIG. 5 illustrates a sample worksheet used for maintaining accreditation data.
Figure 6:
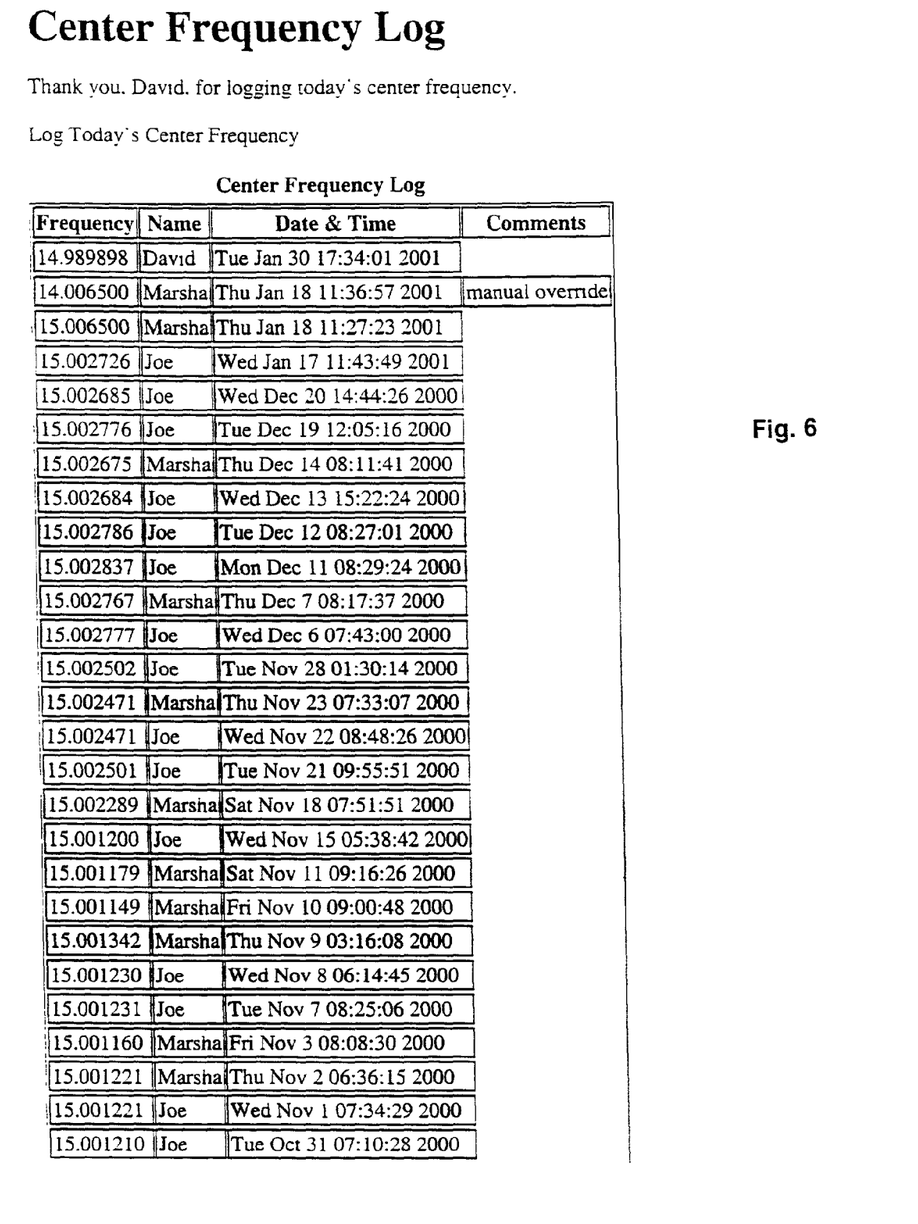
FIG. 6 illustrates a sample log of accreditation data.

While a variety of methods for initiating transmission of information between the central server 21 and the server station 18 are described above, it should be appreciated that various other methods of querying the central server are possible. For example, FTP queries, auto-mailer robots, and the like. As shown in FIG. 5, once the web page for the imaging facility is accessed, the user may be prompted to enter a user name and a central resonant frequency of the imaging unit—which is one of the elements that is required by the ACR for its MRI Accreditation Program. After such information is entered, the information can be saved as a file in within the central server. A record of the user's name, central resonant frequency for the day, and comments can be stored for future retrieval and accreditation purposes (FIG. 6).

In addition to transmitting images and image data, it may also desirable to transmit non-image data to the central server. Physicians and Technologists who have completed continuing medical education ("CME") credits may wish to have their information stored and updated on the server station and central server. Likewise, if maintenance is performed on the imaging unit, it may be desirable to update the records on both the server station memory and the central server 21. Such "non-image data" can be entered by site personnel in a variety of ways. For example, the user can prepare a worksheet, document, or the like noting the maintenance or CME information and thereafter transmit the information to the central server. The non-image information can be transmitted together with the image information or separately from the image information. Alternatively, the user can access the web-page for the imaging facility and manually enter the information into the web site by accessing the web-page dedicated to that particular imaging facility or server station.

Remote monitoring of the imaging unit can be done on a continuous basis so that the central server station 21 can maintain the server station information for the entire accreditation period (which is three years for MRI accreditation). In a specific use, the systems and methods of the present invention are used for monitoring the accreditation status of MRI workstations. The American College of Radiology ("ACR") MRI Accreditation Program has a number of recommendations and requirements that must be monitored at regular intervals in order to get accreditation for the imaging station. Some of the recommendations and requirements are shown in the following chart:

| Item | Frequency | Required or Recommended |
| --- | --- | --- |
| Central resonant frequency | Daily | Required |
| Signal-to-noise ratio (head coil) | Daily | Required |
| Artifact assessment | Daily | Required |
| Statistical review of daily QA measurements | Semi-Annually | Required |
| Image uniformity | Semi-Annually | Required |
| Spatial linearity | Semi-Annually | Required |
| High contrast spatial resolution | Semi-Annually | Required |
| Slice thickness accuracy | Semi-Annually | Required |
| Slice positioning accuracy | Semi-Annually | Required |
| Documentation of film processor sensitometric testing | Weekly | Required |
| Physician CME hours | Continually | Required |
| Technologist CME hours | Continually | Required |
| Scanner service logs | Continually | Required |
| Documented evidence of physician board certification and training | Continually | Required |
| Documented evidence of technologist certification and training | Continually | Required |
| Documented patient screening questionnaire | Continually | Required |
| Documented techniques and indications for each procedure | Continually | Required |
| Documented safety practices and policies | Continually, reviewed at least annually | Required |
| Ghost Intensity | Semi-annually | Recommended |
| Physical and mechanical inspection | Annually | Recommended |
| Interslice RF interference | Annually | Recommended |
| Signal-to-noise ratio (body coil) | Annually | Recommended |
| Signal-to-noise ratio (surface coil) | Annually | Recommended |
| Camera gray scale accuracy | Annually | Recommended |

Data transmitted from the server station 18, such as the data listed in the above chart, can be stored on a local memory 36 and also stored remotely in a memory of the central server 21. If desired, the data stored on the central server can be compiled, analyzed, and prepared for its submission to the accreditation agency. In general, the data from the server station 18 will be compared to the requirements set forth by the accreditation agency to determine if the server station quality is meeting the requirements for accreditation. The personnel at the central server will typically analyze the information on a periodic basis and alert the physicians and technologists of their accreditation status and the facilities maintenance status.

If a variance is found at the site (for example, inadequate phantom imaging quality, etc.) that is not in compliance with the accreditation standards the facility is notified. For example, a user at the central server can send an email or phone call to the personnel at the accreditation site to inform them of the variance. It should be appreciated however, that while it is preferred that the personnel of the central server communicate directly with the personnel of the imaging facility it is also possible to leave a message on the website dedicated to that particular server station to notify the users of the variance or by transmitting an electronic message over the communication network that appears on an output display to notify the personnel of the variance.

By automatically monitoring the requirements, the personnel at the site do not have to keep track of the accreditation requirements on a daily basis. Instead, the central server can maintain a record of all elements that are tracked and a third party can remotely track and inform the personnel of the imaging facility 12 of their accreditation status. If desired, however, the central serve 21 can merely be used to maintain a backup file of the imaging quality information and the analysis and collation of the submission report can be manually prepared or automatically prepared by the computer server station on site (using software for preparation of the accreditation report.

In exemplary methods of the present invention, the personnel at the central server can summarize the information collected from the server station 18 and provide a report on a regular interval, (i.e., daily, monthly, weekly, twice a year, yearly, or the like.) The data from the server station can be analyzed to determine if the clinical images are using the correct imaging parameters, whether the imaging facility is following the accreditation agencies instructions for the phantom, or the like. If desired by the imaging facility, the personnel at the central server can compile and work with the personnel on site to create an accreditation report for submission into the accreditation agency.

On a periodic basis, in addition to the remote monitoring of the imaging facility, personnel of the central server or other third party contractors can be sent to the imaging facility 12 to perform turnkey service for implementing a site certification program. For example, the third party can be present at the imaging facility to assist in the accreditation process (e.g., during the audit of the imaging facility, analysis or preparation of the submission package, remedial measures, or the like). Because the accreditation information can be analyzed offsite (e.g., at the central server or other remote site), a third party can analyze the accreditation information prior to physically visiting the imaging facility. Consequently, the third party will have a better idea as to what remedial actions are necessary prior to visiting the imaging facility, and instead of analyzing all of the accreditation data onsite for the first time, which can be a timely process, the third party can focus on the imaging facilities known deficiencies. Thus, if it is determined that image quality parameters are insufficient, instead of having to sort through all of the stored imaging data on site, the personnel can focus on the relevant parameters and remedy the variant parameters that could prevent ACR certification. If the personnel at the site are lacking the required training, the contractor can discuss the CME requirements with the personnel, and the like.

While all the above is a complete description of the preferred embodiments of the inventions, various alternatives, modifications, and equivalents may be used. For example, it may be possible for the accreditation agency to remotely audit or monitor the status of the imaging facility through the communication network. Additionally, it may also be possible to file the accreditation submission package over the communication network. As will be appreciated by those of ordinary skill in the art, the foregoing description is intended to be illustrative, but not limiting, of the scope of the invention which is set forth in the following claims.

What is claimed is:

1. A method of collecting accreditation information from an imaging facility, the method comprising:
   receiving accreditation information for an imaging facility at a remote server from a computer server station over a communication network, the accreditation information comprising information used to determine compliance of the imaging facility with one or more accreditation standards, the accreditation information comprising one or more images obtained using one or more imaging units at the imaging facility, information related to one or more patient procedures used at the imaging facility, information related to one or more maintenance practices at the imaging facility, and information related to education and certification of personnel at the imaging facility;
   collating the accreditation information received on the remote server; and
   determining, at the remote server, based upon the accreditation information, if the imaging facility is in compliance with the one or more accreditation standards; and
   communicating a result of the determining to the imaging facility, the result identifying a variance from the accreditation requirement if the imaging facility is determined not to be in compliance with the one or more accreditation standards.

2. The method of claim 1 further comprising uploading information prepared based upon the accreditation information to an accreditation agency.

3. The method of claim 1 wherein communicating the information to the imaging analysis comprises transmitting an analysis of the accreditation information to the imaging facility.

4. The method of claim 2 wherein receiving the accreditation information at the remote server from the computer server station comprises receiving the accreditation information periodically at the remote server.

5. The method of claim 1 wherein the computer server station is located at the imaging facility, the method further comprising sending the one or more images from the one or more imaging units to the computer server station.

6. The method of claim 5 wherein an application executing on the computer server station transmits the accreditation information to the remote server.

7. The method of claim 1 wherein the one or more imaging units comprise a Magnetic Resonance Imaging (MRI) device.

8. The method of claim 1 wherein the one or more imaging units comprise an x-ray device, a nuclear medicine device, or a CT device.

9. The method of claim 1 wherein the accreditation information comprises at least one of image reports, central resonant frequency information, kilovoltage information, scattered radiation information, signal-to-noise ratio information, and artifact assessment information.

10. The method of claim 1 wherein the imaging facility comprises the computer server station.

11. The method of claim 10 further comprising querying the computer server station to transmit the accreditation information to the remote server.

12. The method of claim 10 wherein the computer server station is programmed to automatically transmit the accreditation information to the remote server at a preset interval.

13. The method of claim 1 wherein the information related to one or more maintenance practices at the imaging facility comprises one or more maintenance logs for the imaging facility.

14. The method of claim 1 further comprising sending data to the imaging facility alerting personnel of the imaging facility of at least one of a preventive maintenance update and personnel training requirement.

15. The method of claim 1 wherein the network is the internet.

16. The method of claim 1 wherein the receiving comprises automatically receiving the accreditation information at the remote server at a predetermined interval.

17. The method of claim 16 wherein the predetermined interval is daily.

18. The method of claim 16 wherein the predetermined interval is monthly.

19. The method of claim 16 wherein the predetermined interval is six months.

20. The method of claim 1 further comprising accessing a web page over the network to deliver additional data to the remote server.

21. The method of claim 1 further comprising monitoring the imaging facility to check for information included in the accreditation information.

22. The method of claim 1 wherein receiving the accreditation information comprises receiving the accreditation information in encrypted form.

23. The method of claim 1 further comprising preparing an accreditation submission for submission to an accreditation agency.

24. The method of claim 1 further comprising preparing for an accreditation audit for the imaging facility.

25. The method of claim 24 wherein the accreditation audit is prepared based upon the accreditation information.

26. The method of claim 1 wherein:
   the imaging facility is an Magnetic Resonance Imaging (MRI) imaging facility;
   the one or more accreditation standards are American College of Radiology standards; and
   the one or more imaging units comprise an MRI unit.

27. The method of claim 1 wherein the communicating comprises communicating the result to the computer server station.

28. The method of claim 1 wherein the communicating is performed at a regular interval.

29. The method of claim 28 wherein the regular interval is daily, weekly, monthly, bi-annually, or annually.

30. The method of claim 1 wherein the accreditation information comprises image quality information.

31. The method of claim 1 wherein:
   the imaging facility is an CT imaging facility; and
   the one or more imaging units comprise a CT unit.

32. The method of claim 1 wherein the one or more imaging units comprises a nuclear imaging unit.

33. The method of claim 1 wherein the one or more imaging units comprises an X-ray unit.

34. A method for monitoring an imaging facility from a remote location, the method comprising:
  acquiring accreditation information for the imaging facility, the accreditation information comprising information used to determine compliance of the imaging facility with accreditation requirements, the accreditation information comprising an image obtained using a first imaging unit at the imaging facility, information related to one or more patient screening procedures used at the imaging facility, information related to maintenance practices at the imaging facility, and information related to education and certification of personnel at the imaging facility;
  transmitting the accreditation information to a local server station;
  sending the accreditation information from the local server station over a network to a remote server;
  saving the accreditation information on the remote server;
  determining, based upon the accreditation information, if the imaging facility is in compliance with the accreditation requirements; and
  communicating a result of the determining to the imaging facility, the result identifying a variance from the accreditation requirement if the imaging facility is not determined to be in compliance with the accreditation requirements.

35. The method of claim 34 wherein the network is the internet.

36. The method of claim 34 wherein acquiring comprises monitoring at least one of image quality and phantom imaging.

37. The method of claim 34 wherein the accreditation information comprises an image obtained using a second imaging unit at the imaging facility.

38. The method of claim 34 further comprising delivering one or more reminders from the remote server to the imaging facility over the network.

39. The method of claim 34 further comprising compiling an accreditation report at the remote server based upon the accreditation information and transmitting the accreditation report to the local server station over the network.

40. The method of claim 34 wherein the acquiring and the transmitting occurs on a fixed schedule.

41. The method of claim 34 wherein acquiring the accreditation information comprises receiving information regarding a preventive maintenance visit to the imaging facility, or continuing education credits for personnel, or a policy of the imaging facility.

42. A method of monitoring accreditation status of an imaging facility, the method comprising:
  transmitting accreditation information for the imaging facility to a first server, the accreditation information comprising information used to determine compliance of the imaging facility with one or more accreditation standards, the accreditation information comprising one or more images obtained using one or more imaging units at the imaging facility, information related to one or more patient procedures used at the imaging facility, information related to one or more maintenance practices at the imaging facility, and information related to education and certification of personnel at the imaging facility;
  sending the accreditation information from the first server over a network to a second server;
  saving the accreditation information on the second server; and
  determining at the second server, based upon the accreditation information, if the imaging facility is in compliance with the one or more accreditation standards; and
  communicating a result of the determining to the imaging facility, the result identifying a variance from the accreditation requirement if the imaging facility is not determined to be in compliance with the accreditation requirements; and
  uploading the accreditation information to an accreditation agency over a communication network.

43. The method of claim 42 further comprising encrypting the accreditation information at the first server.

44. The method of claim 42 comprising preparing an accreditation submission package prior to uploading.

* * * * *